United States Patent
Hung et al.

(10) Patent No.: US 11,840,729 B2
(45) Date of Patent: Dec. 12, 2023

(54) PORTABLE GENOME SEQUENCING AND GENOTYPING DEVICE AND OPERATING METHOD THEREOF

(71) Applicants: NATIONAL CHIAO TUNG UNIVERSITY, Hsinchu (TW); NATIONAL TAIWAN UNIVERSITY, Taipei (TW)

(72) Inventors: Jui-Hung Hung, Hsinchu (TW); Chia-Hsiang Yang, New Taipei (TW)

(73) Assignees: NATIONAL CHIAO TUNG UNIVERSITY, Hsinchu (TW); NATIONAL TAIWAN UNIVERSITY, Taipei (TW)

( * ) Notice: Subject to any disclaimer, the term of this patent is extended or adjusted under 35 U.S.C. 154(b) by 425 days.

(21) Appl. No.: 17/114,455

(22) Filed: Dec. 7, 2020

(65) Prior Publication Data
US 2022/0017955 A1    Jan. 20, 2022

(30) Foreign Application Priority Data
Jul. 14, 2020    (TW) .................................. 109123665

(51) Int. Cl.
*C12Q 1/6869* (2018.01)
*B01L 3/00* (2006.01)

(52) U.S. Cl.
CPC ...... *C12Q 1/6869* (2013.01); *B01L 3/502707* (2013.01)

(58) Field of Classification Search
CPC .. C12Q 1/6869; B01L 3/502707; G16B 20/00
See application file for complete search history.

(56) References Cited

U.S. PATENT DOCUMENTS

| 5,295,782 A | 3/1994 | Frye, Jr. |
| 7,189,503 B2 | 3/2007 | Akeson et al. |
| 8,673,556 B2 | 3/2014 | Akeson et al. |
| 2009/0046456 A1 | 2/2009 | Urano et al. |
| 2016/0319327 A1 | 11/2016 | Kain et al. |

FOREIGN PATENT DOCUMENTS

| CN | 105886391 A | 8/2016 |
| TW | 201247180 A | 12/2012 |
| TW | I636372 B | 9/2018 |
| WO | WO2017214320 | * 12/2017 |

OTHER PUBLICATIONS

Krehenwinkel et al., Genes, 10, 858, 1-16, (Year: 2019).*

* cited by examiner

*Primary Examiner* — Cynthia B Wilder
(74) *Attorney, Agent, or Firm* — CKC & Partners Co., LLC

(57) ABSTRACT

A portable genome sequencing and genotyping device includes a sample processing module, a sequencing module, an analyzing module, and a communication module. The sample processing module is configured to process a sample so as to generate at least one DNA segment of the sample. The sequencing module is connected to the sample processing module, and is configured to generate a number of base sequences corresponding to the at least one DNA segment. The analyzing module is coupled to the sequencing module, and is configured to generate a genotyping analysis result based on the base sequences. The communication module is configured to receive the genotyping analysis result and transmit the genotyping analysis result to a user terminal.

8 Claims, 2 Drawing Sheets

PORTABLE GENOME SEQUENCING AND GENOTYPING DEVICE AND OPERATING METHOD THEREOF

RELATED APPLICATIONS

This application claims priority to Taiwan Application Serial Number 109123665, filed Jul. 14, 2020, which is herein incorporated by reference.

BACKGROUND

Field of Invention

The present disclosure relates to a genome sequencing and genotyping device and an operating method thereof. More particularly, the present disclosure relates to a totally portable genome sequencing and genotyping device and an operating method thereof.

Description of Related Art

The current genome sequencing related devices mostly need to perform specific steps respectively on different devices. In addition, when a genotyping analysis is performed, data must be uploaded to the cloud to proceed because a large amount of memory computing resources are required, and the genotyping analysis can not be collectively completed on a same device.

For the forgoing reasons, there is a need to provide a portable genome sequencing and genotyping device and an operating method thereof to solve the above-mentioned problems.

SUMMARY

In order the resolve the above-mentioned problems, the present disclosure provides a portable genome sequencing and genotyping device comprising a sample processing module, a sequencing module, an analyzing module, and a communication module. The sample processing module is configured to process a sample so as to generate at least one DNA segment of the sample. The sequencing module is connected to the sample processing module. The sequencing module is configured to generate a plurality of base sequences corresponding to the at least one DNA segment. The analyzing module is coupled to the sequencing module. The analyzing module is configured to generate a genotyping analysis result based on the plurality of base sequences. The communication module is configured to receive the genotyping analysis result, and transmit the genotyping analysis result to a user terminal.

Another aspect of the present disclosure provides an operating method of a portable genome sequencing and genotyping device comprising the following steps: obtaining a plurality of signals corresponding to a sample; converting the plurality of signals into a genome sequence; analyzing the genome sequence to generate a genotyping analysis result; and transmitting the genotyping analysis result to a user terminal.

It is to be understood that both the foregoing general description and the following detailed description are by examples, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

DESCRIPTION OF THE EMBODIMENTS

All terms used herein have their ordinary meanings. The above terms are defined in the commonly used dictionaries, and any examples of the use of the term discussed herein included in the description of the present specification are merely for illustrative purposes, and are not intended to limit the scope and meaning of the present disclosure. Similarly, the present disclosure is not limited to the various embodiments described in this specification.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present disclosure. It will be understood that, as used herein, the phrase "and/or" includes any and all combinations of one or more of the associated listed items.

In this document, the term "coupled" may also be termed as "electrically coupled," and the term "connected" may be termed as "electrically connected." "Coupled" and "connected" may mean "directly coupled" and "directly connected" respectively, or "indirectly coupled" and "indirectly connected" respectively. "Coupled" and "connected" may also be used to indicate that two or more elements cooperate or interact with each other.

Figure 1:
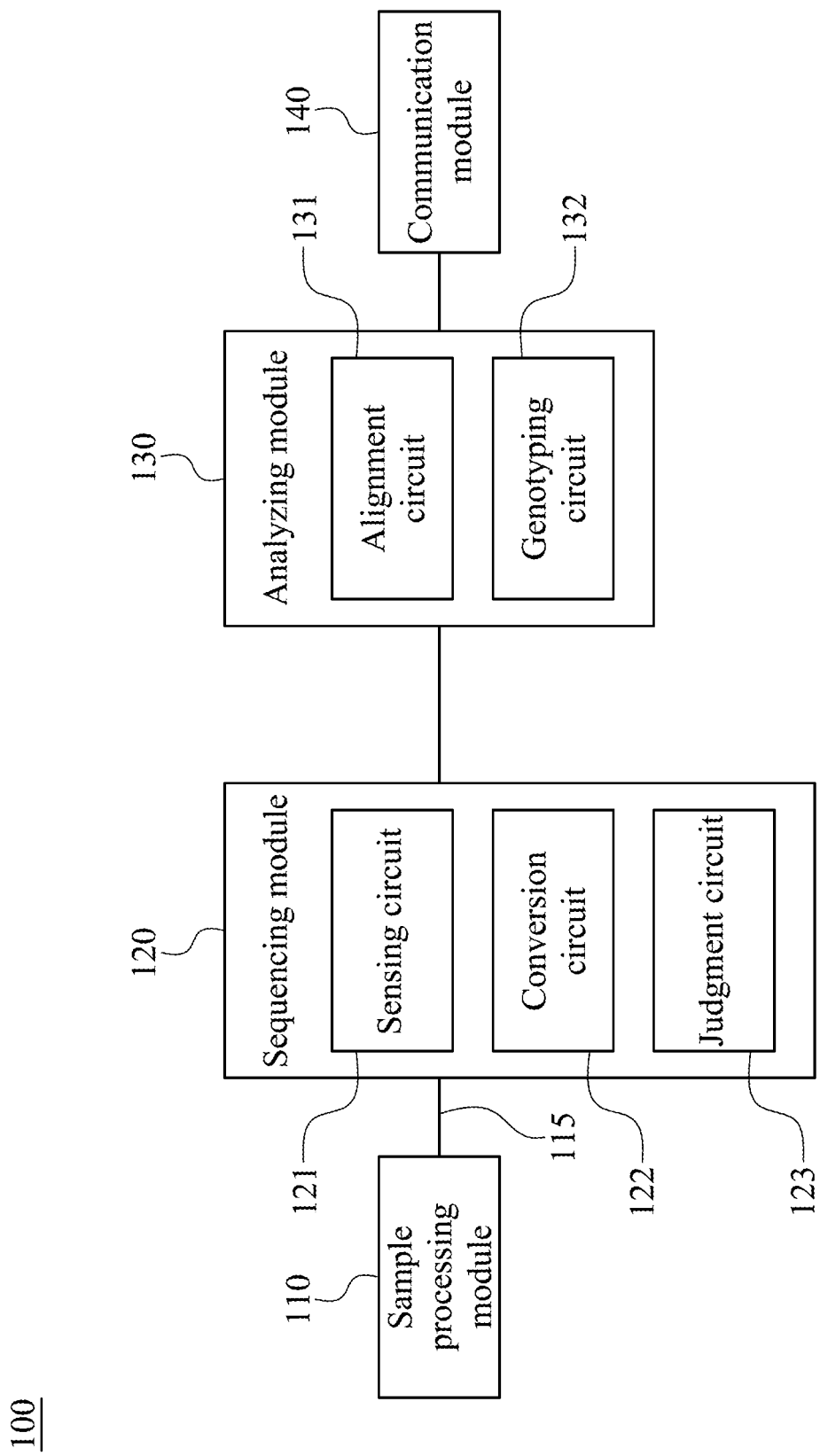
FIG. 1 depicts a schematic diagram of a portable genome sequencing and genotyping device according to one embodiment of the present disclosure.

A description is provided with reference to FIG. 1. FIG. 1 depicts a schematic diagram of a portable genome sequencing and genotyping device 100 according to one embodiment of the present disclosure. As shown in FIG. 1, the portable genome sequencing and genotyping device 100 comprises a sample processing module 110, a sequencing module 120, an analyzing module 130, and a communication module 140.

In some embodiments, the sample processing module 110 is configured to process a sample. By using one or more reagents, at least one purified double-stranded or unwound single-stranded deoxyribonucleic acid (hereinafter referred to as DNA) segment is extracted from a sample, so that it can be utilized during the subsequent genome sequencing.

In some embodiments, the sample is any that can be used to obtain DNA, such as blood, saliva, a tissue, a cell, etc. However, the present disclosure is not limited in this regard.

In some embodiments, the one or more reagents are mixed with the sample in the sample processing module 110 to further purify and amplify the sample, break the cell, and the like. In greater detail, each of the reagents may comprise a helicase used for unwrapping the double-stranded DNA, a lysate used for breaking the cell, a protease used for decomposing a protein, an endonuclease used for cleaving the DNA into multiple segments, etc.

In some embodiments, the sample processing module 100 is connected to the sequencing module 120 through a channel 115. In some embodiments, the channel 115 is a micro-channel. In order to control the sample to be able to move in a predetermined direction in the sample processing module 110 and the micro-channel, each of the above reagents may comprise one or more magnetic beads in some embodiments. By mixing the one or more reagents comprising the magnetic beads with the sample and applying a magnetic field by a control circuit, the sample can be controlled to move in a predetermined direction of the magnetic field. In some embodiments, an electro-wetting method may be used to apply a voltage by the control circuit so as to change hydrophilicity of an electrode. In this manner, a movement direction of the sample is controlled.

In some embodiments, the sequencing module 120 is configured to generate a number of base sequences corresponding to the above at least one DNA segment. In other words, the DNA segment (such as double helix DNA or one of the unwounded strands) extracted from the sample is utilized to generate genome sequence(s) corresponding to the DNA segment composed of a number of bases through steps, such as nanopore sequencing, signal processing, etc. In some embodiments, the above single-stranded DNA may be a complete piece of DNA, or it may be constituted by multiple segments that have been cleaved.

It is noted that although the portable genome sequencing and genotyping device 100 according to the present disclosure only performs genome sequencing and genotyping analysis on single-stranded DNA in the subsequent description, nitrogenous base sequence(s) of another strand of DNA that has not been sequenced in the double-stranded DNA of the original sample can be known by utilizing correspondences between nitrogenous bases in the DNA (for example, Adenine (abbreviated as A) corresponds to Thymine (abbreviated as T), Cytosine (abbreviated as C) corresponds to Guanine (abbreviated as G)). After knowing the nitrogenous base sequence(s) of the single-stranded DNA through the subsequent operations (for example, Adenine (abbreviated as A) corresponds to Thymine (abbreviated as T), Cytosine (abbreviated as C) corresponds to Guanine (abbreviated as G)), the nitrogenous base sequence(s) of the another strand of DNA that has not been sequenced in the double-stranded DNA of the original sample can be known.

In some embodiments, the sequencing module 120 comprises a sensing circuit 121, a conversion circuit 122, and a judgment circuit 123. After the sequencing module 120 receives one or more purified DNA segments (such as the single-stranded DNA) sent from the sample processing module 110, the sensing circuit 121 can be utilized to sense signals generated by passing the one or more purified DNA segments through a nanopore. The different nitrogenous bases in the DNA segment generate different signals correspondingly. In some embodiments, each of the signals is a current signal in an analog form, which can be converted into a digital signal by using the conversion circuit 122. In some embodiments, the above nanopore may be a solid-state nanopore, a biological nanopore formed by protein aggregation, or a hybrid nanopore.

In some embodiments, the sequencing module 120 can perform denoising processing on the signals before or after converting the received signals into a digital format.

In some embodiments, the sequencing module 120 can use the judgment circuit 123 to perform processes, such as base sequence reading and sequence error correcting, etc., to generate the number of base sequences corresponding to the above signals. In greater detail, base sequence reading is to read each of the number of nitrogenous bases comprised in the one or more DNA segments belongs to which of A, T, C, or G, and then sequence error correcting is used to determine whether the read base sequences have errors or not and correct them through similarity between the genome sequences composed of the nitrogenous bases in each of the DNA segments.

In some embodiments, the analyzing module 130 is coupled to the sequencing module 120, and receives the sensed signals or the converted digital signals from the sequencing module 120. In some embodiments, the analyzing module 130 may be formed by a chip, and has a high-speed sequencing (i.e., base calling) and short-segment genome mapping system, which can greatly accelerate the establishment of data structures and reduce memory requirements.

In some embodiments, the analyzing module 130 comprises an alignment circuit 131 and a genotyping circuit 132. After being processed by the sequencing module 120, the portable genome sequencing and genotyping device 100 only obtains the DNA segments that comprise the genome sequences constituted by base sequence information, and it is necessary to further use the alignment circuit 131 in the analyzing module 130 to compare the above base sequences with a reference sequence to calculate an alignment and a position of each of the genome sequences (such as the chromosome to which it belongs and its position on that chromosome). In some embodiments, the alignment circuit 131 can establish an index data structure, such as a hash table or an FM-index, and perform a quick search or LF-mapping operation on part of contents of the genome segments to be searched to obtain a perfectly matched reference sequence correspondingly, and then cooperate with a pairwise alignment circuit to calculate an alignment result comprising the complete sequence and the corresponding reference sequence so as to obtain the exact position of the sequence in the reference sequence.

In some embodiments, the genotyping circuit 132 is configured to further analyze information, such as an actual genotype or a content combination at a same locus of each of the above genome sequences. In greater detail, the genotyping circuit 132 can perform steps, comprising pre-processing (including ranking, filtering, correcting, etc.), haplotype recombination, variant calling, and genotyping, on the sequences corresponding to specific regions to calculate the variant loci and genotypes. By using the above analytical and comparison method, the genotype identification is performed and the possible genetic variation can be obtained. For example, the genotyping circuit 132 can compare the genome sequences in the sequenced DNA segments with a reference gene and perform the above analysis to find variations in the DNA sequences, such as base insertion, base deletion, and single nucleotide polymorphism (SNP), etc., and generate a genotyping analysis result.

In some embodiments, the communication module 140 receives the genotyping analysis result generated by the analyzing module 130, and transmits it to a user terminal for further observation or diagnosis by a user or a medical researcher. In some embodiments, a file format of the comparison result may be a variant call format (VCF) or any storage format that can be used for storing the genetic mutation data of the comparison result. In some embodiments, the communication module 140 may be a communication module that transmits in a wireless manner, such as a Bluetooth module, a Wi-fi module, and the like, or a communication module, such as a USB that transmits through a wired network in a wired manner, etc. However, the present disclosure is not limited in this regard. In some embodiments, the user terminal may be a mobile phone, a tablet computer, a desktop computer, a notebook computer, etc., and the present disclosure is not limited in this regard.

In summary, the portable genome sequencing and genotyping device 100 according to the present disclosure can complete the genome sequencing on a same device that is easy to carry and lightweight, thus eliminating the complicated process flow caused by combining multiple devices. In addition, there is no need to upload data to the cloud, but the calculation and analysis are directly performed locally. In this manner, the genome sequencing and genotyping device can be fully portable.

Figure 2:
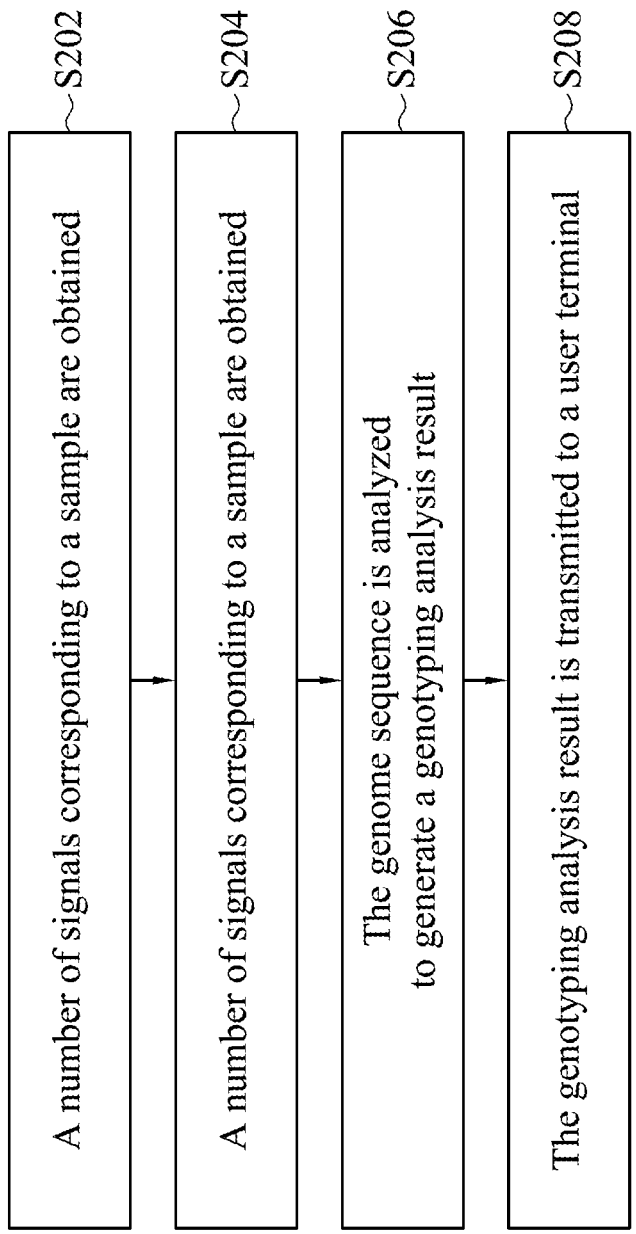
FIG. 2 depicts a flowchart of an operating method of a portable genome sequencing and genotyping device according to one embodiment of the present disclosure.

A description is provided with reference to FIG. 2. FIG. 2 depicts a flowchart of an operating method 200 of a portable genome sequencing and genotyping device according to one embodiment of the present disclosure. As shown in FIG. 2, the operating method 200 comprises step S202, step S204, step S206, and step S208.

In step S202, a number of signals corresponding to a sample are obtained. In some embodiments, this operation is to pass double strands or one strand of DNA through a channel to generate current signals correspondingly. In some embodiments, the generated analog current signals can be further converted into digital signals. In some embodiments, human blood can be used as the sample, and double-stranded DNA in the blood is decomposed and purified into a single-stranded DNA form for subsequent analysis operations by using the portable genome sequencing and genotyping device.

In step S204, the number of signals generated by a sequence are converted into a genome sequence. In some embodiments, the above genome sequence is a base sequence of human DNA, which is composed of letters or codes corresponding to four bases.

In step S206, the above genome sequence is analyzed to generate a genotyping analysis result. In some embodiments, the genome sequence can be compared with a reference gene and a genotyping calculation can be performed to calculate the variant loci and genotypes that exist in the genome sequence in the sample.

In step S208, the genotyping analysis result is transmitted to a user terminal by utilizing a wired or wireless communication method for a further professional evaluation (for example, medical diagnosis of causes or symptoms of a specific genetic variation, etc.).

In some embodiments, the operation of obtaining the number of signals corresponding to the sample in the operating method 200 of the portable genome sequencing and genotyping device comprises separating one or more purified DNA segments from the sample by utilizing one or more reagents, and obtaining the corresponding signals generated by passing the one or more purified DNA segments through the channel.

In some embodiments, the operation of separating the one or more purified DNA segments from the sample in the operating method 200 of the portable genome sequencing and genotyping device comprises a purification process of adding a reagent, such as an enzyme, a protease, etc., to the sample to break a cell wall, decompose a protein, and the like, so as to extract the DNA from the sample, and cleaving the sample into multiple DNA segments for signal reading.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A portable genome sequencing and genotyping device comprising:
    a sample processing module configured to process a sample so as to generate at least one DNA segment of the sample;
    a sequencing module connected to the sample processing module, the sequencing module being configured to generate a plurality of base sequences corresponding to the at least one DNA segment;
    an analyzing module coupled to the sequencing module, the analyzing module being configured to generate a genotyping analysis result based on the base sequences;
    a communication module configured to receive the genotyping analysis result, and transmit the genotyping analysis result to a user terminal; and
    a micro-channel connected between the sample processing module and the sequencing module, wherein the micro-channel transmits the at least one DNA segment to the sequencing module in a predetermined direction by using a control circuit.

2. The portable genome sequencing and genotyping device of claim 1, wherein the sample comprises at least one reagent, the at least one reagent is used to separate the at least one DNA segment from the sample that is purified.

3. The portable genome sequencing and genotyping device of claim 2, wherein the sequencing module comprises:
    a sensing circuit configured to generate a plurality of signals corresponding to the at least one DNA segment in the sample based on current changes corresponding to the at least one DNA segment;
    a conversion circuit configured to convert the signals from an analog form to a digital form; and
    a judgment circuit configured to generate the base sequences corresponding to the signals.

4. The portable genome sequencing and genotyping device of claim 1, wherein the analyzing module is configured to obtain an alignment result and a position result of each of the base sequences generated by the sequencing module corresponding to a reference sequence, and use the alignment result and the position result to calculate a genotype that each of a plurality of loci in the base sequences has.

5. The portable genome sequencing and genotyping device of claim 1, wherein the analyzing module comprises:
    an alignment circuit configured to generate an alignment result and a position result corresponding to a reference sequence based on the base sequences; and
    a genotyping circuit configured to perform a genotyping analysis based on the alignment result.

6. An operating method for the portable genome sequencing and genotyping device of claim 1 comprising:
    obtaining a plurality of signals corresponding to a sample, wherein the operation of obtaining the plurality of signals corresponding to a sample comprises: utilizing the micro-channel to transmit at least one DNA segment of the sample in a predetermined direction by using the control circuit;

converting the signals into a genome sequence;
analyzing the genome sequence to generate a genotyping analysis result; and
transmitting the genotyping analysis result to the user terminal.

7. The operating method of claim 6, wherein the operation of obtaining the plurality of signals corresponding to a sample comprises:
utilizing at least one reagent to separate at least one purified DNA segment from the sample; and
obtaining the signals corresponding to the at least one DNA segment.

8. The operating method of claim 7, wherein the operation of separating the at least one purified DNA segment from the sample comprises:
removing an excessive impurity in the sample, wherein the impurity comprises a protein;
cleaving the sample into a plurality of DNA segments; and
separating the DNA segments that are purified from the sample.

* * * * *